US011452309B2

(12) United States Patent
Paluszkiewicz et al.

(10) Patent No.: US 11,452,309 B2
(45) Date of Patent: Sep. 27, 2022

(54) FORMULA OF PREPARATIONS FOR ORAL AND/OR ENTERAL FEEDING OF CHILDREN

(71) Applicants: Mariusz Trus, Lublin (PL); Piotr Paluszkiewicz, Lublin (PL); Pawel Milart, Lublin (PL); Waldemar Turski, Lublin (PL)

(72) Inventors: Piotr Paluszkiewicz, Lublin (PL); Pawel Milart, Lublin (PL); Waldemar Turski, Lublin (PL)

( * ) Notice: Subject to any disclaimer, the term of this patent is extended or adjusted under 35 U.S.C. 154(b) by 232 days.

(21) Appl. No.: 16/479,119

(22) PCT Filed: Jan. 16, 2018

(86) PCT No.: PCT/PL2018/000006
§ 371 (c)(1),
(2) Date: Jul. 18, 2019

(87) PCT Pub. No.: WO2018/135957
PCT Pub. Date: Jul. 26, 2018

(65) Prior Publication Data
US 2019/0387782 A1    Dec. 26, 2019

(30) Foreign Application Priority Data

Jan. 20, 2017  (PL) .......................................... 420258

(51) Int. Cl.
*A23L 33/175* (2016.01)
*A23L 33/00* (2016.01)
(52) U.S. Cl.
CPC ............. *A23L 33/175* (2016.08); *A23L 33/40* (2016.08)
(58) Field of Classification Search
CPC ............................... A23L 33/175; A23L 33/40
USPC ......................................... 426/656, 580, 648
See application file for complete search history.

(56) References Cited

FOREIGN PATENT DOCUMENTS

WO    2006/117624 A2    11/2006
WO    2008/087461 A2    7/2008

OTHER PUBLICATIONS

O'Rourke L. et al. "The Relationship Between Maternal Tryptophan Metabolism, Cytokines and Cortisol in Term and Preterm Expressed Breast Milk" 2014 Pediatric Academic Societies and Asian Society for Pediatric Research Joint Meeting in Vancouver, BC, Canada, May 3-6 Retrieved from http://undergraduatelibrary.org/system/files/1251.pdf.
Walczak, K.: "Nowe aspekty aktywnosci biologicznej kwasu kynureninowego, produktu katabolizmu tryptofanu" Medycyna Ogolna, 2009, 15 (XLIV), 4, p. 566-575.
Turski, M.P. et al. "Kynurenic Acid in the Digestive System—New Facts, New Challenges" Int J Tryptophan Res. Sep. 4, 2013;6:47-55.
International Search Report issued for PCT/PL2018/000006, dated May 14, 2018.
Written Opinion of International Searching Authority issued for PCT/PL2018/000006, dated May 14, 2018.
Kuc et al. "Micromolar concentration of kynurenic acid in rat small intestine" Amino Acids. 2008, 35: 503-5).
Kemp et al. "7Chlorokynurenic acid is a selective antagonist at the glycine modulatory site of the N-methyl-D-aspartate receptor complex" Proc Natl Acad Sci USA, 1988, 85: 6547-6550.
Hilmas et al. "The Brain Metabolite Kynurenic Acid Inhibits α7 Nicotinic Receptor Activity and Increases Non-α7 Nicotinic Receptor Expression: Physiopathological Implications" J Neurosci, 2001, 21: 7463-7473.
Glavin et al. "Kynurenic acid protects against gastroduodenal ulceration in mice injected with extracts from poisonous atlantic shellfish" Prog Neuropsychopharmacol Biol Psychiatry. 1989; 13(3-4):569-72, Res Commun Chem Pathol Pharmacol. 1989;64:111-9.
DiNatale et al. "Kynurenic Acid Is a Potent Endogenous Aryl Hydrocarbon Receptor Ligand that Synergistically Induces Interleukin-6 in the Presence of Inflammatory Signaling" 2010, Toxicol Sci. 2010; 115:89-97.
Kaszaki et al. "Kynurenic acid inhibits intestinal hypermotility and xanthine oxidase activity during experimental colon obstruction in dogs" Neurogastroenterol Motil, 2008, 20, 53-62.
Nasstrom et al. "Antinociceptive actions of different classes of excitatory amino acid receptor antagonists in mice" Eur J Pharmacol, 1992, 212, 21-9.
Turski et ai. "Presence of kynurenic acid in food and honeybee products" Amino Acids. 2009; 36: 75-80.
Turski et al. "On the toxicity of kynurenic acid in vivo and in vitro" Pharmacol Rep. 2014;66:1127-1133.
Wang et al. "Kynurenic Acid as a Ligand for Orphan G Protein-coupled Receptor GPR35" 2006, J Biol Chem, 281:22021-22028.
Zgrajka et al. "Kynurenic acid content in anti-rheumatic herbs" Ann Agric Environ Med. 2013; 20: 800-802.
Glavin et al. "Kynurenic acid attenuates experimental ulcer formation and basal gastric acid secretion in rats" Res Commun Chem Pathol Pharmacol Apr. 1989; 64(1):111-119.
Buttar, H.S et al.: "Evaluation of the antioxidant properties of tryptophan and its metabolites in in vitro assai" Journal of Complementary & Integrative Medicine (Jun. 1, 2016) vol. 13, No. 2, pp. 129-136 (Abstract).
Hottinger, A. et al. "The excretion of xanthurenic acid and kynurenic acid after a tryptophan load" Internationale Zeitschrift fuer Vitaminforschung (1963), 34(1), 99. 81-8 (Abstract).

(Continued)

*Primary Examiner* — Helen F Heggestad
(74) *Attorney, Agent, or Firm* — Westman, Champlin & Koehler, P.A.; Z. Peter Sawicki; Amanda M. Prose

(57) ABSTRACT

The subject of the invention is a new and improved formula of preparations for the oral and enteral feeding of children and offspring of mammals, which cannot or should not be fed by the mother, characterized by the fact, that the preparations contain kynurenic acid or its salt at a concentration adapted to its content in the mother's natural milk at different times from delivery.

4 Claims, No Drawings

(56) References Cited

OTHER PUBLICATIONS

Cruz, M., et al. "Urinary excretion of metabolites of the tryptophan-kynurenine pathway in healthy infants after an oral loading dose of L-tryptophan" Revista Espanola de Fisiologia (1972), 28(4), pp. 283-286 (Abstract).
Search Report issued in PL patent application No. 420258, dated Aug. 9, 2017.
International Preliminary Report on Patentability issued for PCT/PL2018/000006, dated Jul. 23, 2019.

FORMULA OF PREPARATIONS FOR ORAL AND/OR ENTERAL FEEDING OF CHILDREN

CROSS-REFERENCE TO RELATED APPLICATION

This application is a Section 371 National Stage Application of International Application No. PCT/PL2018/000006, filed Jan. 16, 2018, and published as WO2018/135957A1 on Jul. 26, 2018, which claims priority to and benefits of Polish Patent Application Serial No. P.420258, filed with the Patent Office of the Republic of Poland on Jan. 20, 2017, the entire contents of which are incorporated herein by reference.

The subject of the invention is a new and improved formula for the oral and enteral feeding of children and offspring of mammals characterised by the fact that the preparations contain kynurenic acid or its salt at a concentration adapted to its content in the breast milk at different times from birth.

The correct development of the child (including postnatal maturation of various organs and systems) is to a large extent dependent on a balanced supply of food understood as a biologically active mixture of basic nutrients, minerals, vitamins, and substances found in trace amounts, responsible for enabling a bridging transition between the prenatal period and the intake of solid foods. In developmental physiology, it is assumed that the ideal composition of the mixture is provided in the human breast milk which composition changes with the development of the fed baby. The inability of the mother to feed her baby due to the lack of lactation, diseases of the mammary glands (lactic in animals) or dysfunctions of the newborn which prevent natural feeding, requires the use of special feeding techniques such as enteral nutrition by a gastric tube (nutritional fistula), or the provision of substitute food. The composition of substitute foods is designed to deviate in the minimum amount possible from the composition of the nursing mother's breast milk. According to data from the World Health Organization, only 38% of children are breastfed by mothers. Approximately 800,000 infant deaths caused by suboptimal feeding are recorded annually, including due to the use of mixtures replacing the mother's breast milk. Despite the progress in research on the composition of milk provided by nursing mothers, it was considered that the optimal solution is to introduce a policy promoting natural feeding and the goal is to reach a percentage of 50% of children fed by mothers in a natural way by 2025. This policy is a response to the insufficient progress in the development of new nutrient mixtures, which can replace natural human breast milk.

Additionally, it is emphasised that natural feeding by mothers plays a significant role in reducing the risk of diseases in adulthood, such as obesity, diabetes and asthma (*WHO Global Targets* 2025, www.who.int).

When conducting research on the development of the gastrointestinal tract, it was unexpectedly found that kynurenic acid is present in the human breast milk in varying amounts, dependent on the time elapsed since delivery. It was stated that the concentration of kynurenic acid in milk increases with time.

Kynurenic acid is a metabolite of tryptophan formed on the kynurenine pathway. It occurs in the tissues and body fluids in the human body and in other mammals. It is absorbed from the gastrointestinal tract and reaches high levels in the blood and tissues (Kuc et al. *Amino Acids.* 2008, 35: 503-5).

Kynurenic acid has an effect on glutamate receptors, such as the N-methyl-D-aspartic (NMDA) receptor, the kainate receptor, and the α-amino-3-hydroxy-5-methyl-4-isoxazole-propionic (AMPA) receptor. Kynurenic acid is an antagonist of the nicotinic alpha-7 receptor (Kemp et al. *Proc Natl Acad Sci USA,* 1988, 85: 6547-50; Hilmas et al. *J Neurosci,* 2001, 21: 7463-73). In addition, it affects the GPR35 receptor (Wang et al. 2006, *J Biol Chem,* 281: 22021-8) and the AHR receptor (DiNatale et al. 2010, *Toxicol Sci.* 2010; 115:89-97). The GPR35 and AHR receptors are particularly abundantly present in the gastrointestinal tract.

Kynurenic acid is known to inhibit the development of oxidative stress and prevent lipid peroxidation in intestinal obstruction (Kaszaki et al. *Neurogastroenterol Motil,* 2008, 20, 53-62). Kynurenic acid also has an analgesic effect (Nasström et al. *Eur J Pharmacol,* 1992, 212, 21-9).

The protective effect of kynurenic acid against gastric ulcers is also known (Glavin et al. *Prog Neuropsychopharmacol Biol Psychiatry.* 1989; 13(3-4):569-72, *Res Commun Chem Pathol Pharmacol.* 1989; 64:111-9).

Kynurenic acid and its derivatives are used for the preparation of medicaments used in the treatment of disease states with increased intestinal peristalsis (Kaszaki et al. *Neurogastroenterol Motil,* 2008, 20, 53-62), and also in gout and multiple sclerosis (WO/2008/087461). Kynurenic acid is also effective in the treatment of septic shock (WO/2006/117624).

Because kynurenic acid occurs in plants, including herbs for medical applications (Zgrajka et al., *Ann Agric Environ Med.* 2013; 20: 800-2) and in food, mainly of vegetable origin (Turski et al., *Amino Acids.* 2009; 36:75-80) and does not show any toxic effects (Turski et al., *Pharmacol Rep.* 2014; 66:1127-33) it was examined what the content of this substance is in known preparations for oral feeding of children. It was unexpectedly found that none of the producers indicates the presence of kynurenic acid in their product. In professional literature, there is no information on the content of kynurenic acid in preparations used for children's nutrition. Our own research indicated that in the currently manufactured preparations, the amount of kynurenic acid is very diverse and only in some preparations intended for children up to 6 days of age approaches the physiological quantities of kynurenic acid during this period. In addition, it has been determined that that the amount of kynurenic acid in modern preparations for children's nutrition is not controlled in a planned manner and is accidental. It probably results from the use of various natural ingredients in the preparation process. On this basis, it can be stated that the presence of kynurenic acid in current preparations for child nutrition can be regarded as accidental "contamination". In view of the well-defined biological effect of kynurenic acid and the fact that its content in the natural milk of breastfeeding women varies in depending on the time, an improved composition of preparations intended for children's nutrition was proposed, in which natural changes in the content of kynurenic acid in breast milk were taken into account.

EXAMPLES

Material Human Breast Milk

Milk from 25 breastfeeding mothers was used for testing. Each mother provided a sample of 10 ml of fresh milk independently drawn by the nursing mother into a sterile test tube. Milk samples were taken from each mother 6 times on the third day, after one week, two weeks, one month, three months and six months after physiological labour.

Formulas Intended for the Oral Feeding of Infants

Standard formulas intended for oral feeding of infants up to 6 months of age were obtained commercially. Three packages of a commercial preparation were used for the study from each of the three analysed different series specified by the manufacturer on the packaging.

Methods

The 0.1 ml of 2 M perchloric acid was added to every 0.5 ml of human breast milk samples and centrifuged for 15 minutes at 6000 rpm. The obtained supernatant was stored at $-20°$ C. to determine the concentration of kynurenic acid.

Samples of formulas intended for feeding infants up to 6 months of age were prepared in accordance with the recipe provided by the manufacturer. Perchloric acid was added to liquid formula samples and the mixture was centrifuged like milk from nursing mothers. The obtained supernatant was used for further determinations.

The supernatant was acidified with 2 M trichloric acid. The denatured proteins were separated by centrifugation and the obtained deproteinized supernatant was suspended in 1 M hydrochloric acid.

The obtained deproteinized supernatant was applied to ion-exchange columns (Dowex 50W+, 200-400 mesh) filled with 0.1 M hydrochloric acid. The columns were washed with 1 ml 0.1 M HCl and 1 ml of deionized water. The obtained eluate was chromatographed (HPLC). The quantitative determination of kynurenic acid was carried out using the metric fluoride technique. The kynurenic acid standard was obtained from Sigma-Aldrich (St. Louis, USA). All reagents used to determine the kynurenic acid concentration came from the producers providing the highest degree of purity.

Results

Example 1

The Concentration of Kynurenic Acid in the Human Breast Milk

As a result of the research, an increasing concentration of kynurenic acid in the human breast milk was found depending on the time elapsed from delivery. The average concentration of kynurenic acid in breast milk on the third day after delivery was 14 times lower than the average concentration after 6 months of breastfeeding (Table 1). The observed differences were statistically significant from the 14th day after delivery compared to the content on the 3rd day.

TABLE 1

The concentration of kynurenic acid ($\mu$g/100 ml) in the human breast milk depending on the time passed since the delivery.

| | Time passed since the delivery | | | | | |
|---|---|---|---|---|---|---|
| | 3 × 24 hours | 6 × 24 hours | 2 weeks | 4 weeks | 3 months | 6 months |
| arithmetic mean | 0.39 | 1.07 | 2.11 | 3.74 | 4.15 | 5.66 |
| SD | 0.34 | 1.26 | 1.79 | 2.28 | 2.68 | 3.34 |
| SEM | 0.06 | 0.23 | 0.34 | 0.45 | 0.55 | 0.86 |
| Median | 0.30 | 0.59 | 1.70 | 2.99 | 3.16 | 5.18 |
| Min | 0.00 | 0.00 | 0.34 | 0.45 | 0.37 | 0.83 |
| Max | 1.53 | 4.88 | 9.24 | 10.36 | 11.03 | 13.78 |
| ANOVA Dunn post-hoc test | | NS | $p < 0.01$ | $p < 0.001$ | $p < 0.001$ | $p < 0.001$ |

SD - standard deviation;
SEM - standard error of the mean;
min - lowest;
max - the highest measurement value Example 2

The concentration of kynurenic acid in commercial preparations of milk intended for feeding newborns, infants and older children No producer specifies the content of kynurenic acid in the formulations they produce. The conducted tests revealed the presence of kynurenic acid in all tested milk preparations intended for feeding infants (Table 2). As a result of the analyses performed, no differences were found in kynurenic acid content in the tested preparations depending on the packaging from the same manufacturer's series. There were significant differences between the preparations of different manufacturers. The largest difference concerned NAN AR (0.03 $\mu$g/100 ml) and Bebilon 1 immuno fortis (1.08 $\mu$g/100 ml), indicating a 36-fold difference in the amount of kynurenic acid (Table 2).

TABLE 2

The average content of kynurenic acid ($\mu$g/100 ml) in commercial preparations of milk intended for feeding to children depending on the feeding period recommended by the producer.

| Feeding period | since birth | since 4 months | since 6 months | since 9-10 months | since 12 months | since 24 months |
|---|---|---|---|---|---|---|
| NAN AR | 0.03 | | | | | |
| NAN pro HA 1 liquid | 0.07 | | | | | |
| NAN HA 1 | 0.09 | | | | | |
| Bebilon 1 HA immuno fortis | 0.21 | | | | | |
| NAN Active 1 | 0.24 | | | | | |
| Bebiko HA 1 | 0.25 | | | | | |
| NAN 1 | 0.25 | | | | | |
| NAN Pro 1 liquid | 0.31 | | | | | |
| Bebilon Pepti liquid | 0.33 | | | | | |
| Bebilon 1 immuno fortis comfort | 0.33 | | | | | |

TABLE 2-continued

The average content of kynurenic acid (µg/100 ml) in commercial preparations of milk intended for feeding to children depending on the feeding period recommended by the producer.

| Feeding period | since birth | since 4 months | since 6 months | since 9-10 months | since 12 months | since 24 months |
|---|---|---|---|---|---|---|
| Bebilon pepti 1 | 0.35 | | | | | |
| NAN AR | 0.37 | | | | | |
| Bebilon 1 liquid | 0.44 | | | | | |
| Bebilon AR 1 | 0.63 | | | | | |
| Nutramigen 1 | 0.66 | | | | | |
| Enfamil Premium 1 | 0.67 | | | | | |
| Bebiko Nenatal Premium | 0.85 | | | | | |
| Enfamil AR 1 | 0.89 | | | | | |
| Bebiko 1 | 0.93 | | | | | |
| HIPP BIO 1 | 1.03 | | | | | |
| Bebilon 1 immuno fortis | 1.08 | | | | | |
| Bebilon PEPTI 2 | | 0.38 | | | | |
| Nutramigen 2 | | 0.58 | | | | |
| Bebilon HA 2 | | | 0.29 | | | |
| NAN HA 2 | | | 0.31 | | | |
| Bebiko HA 2 | | | 0.33 | | | |
| Bebilon comfort 2 | | | 0.47 | | | |
| NAN 2 | | | 0.54 | | | |
| Bebiko 2R | | | 0.70 | | | |
| Bebiko 2 | | | 0.71 | | | |
| NAN 2 R | | | 0.71 | | | |
| NAN 2 Active | | | 0.74 | | | |
| Enfamil premium 2 | | | 0.80 | | | |
| NAN pro d.noc B | | | 0.95 | | | |
| Bebilon 2 immuno fortis | | | 0.99 | | | |
| Enfamil AR 2 | | | 1.19 | | | |
| HIPP BIO 2 | | | 1.42 | | | |
| NAN HA 3 | | | | 0.28 | | |
| NAN PRO 3 | | | | 0.98 | | |
| NAN 3R | | | | 1.08 | | |
| HIPP BIO 3 | | | | 1.52 | | |
| Bebiko Junior 3 | | | | | 0.65 | |
| Bebilon Junior 3 | | | | | 1.18 | |
| Bebiko Junior 4 | | | | | | 0.67 |
| Bebilon Junior 4 | | | | | | 1.03 |

The measurements were made in five milk packages and three different producer's series were compared (15 measurements for each tested preparation).

A comparison of series of the same commercial preparations of milk intended for child nutrition showed significant differences in the content of kynurenic acid. The discrepancy between the series reached twice the amount of kynurenic acid calculated per 100 ml of the preparation intended for children (Table 3).

TABLE 3

The concentration of kynurenic acid (µg/100 ml) in the tested milk preparations intended for feeding children with the indication of the series with the lowest and highest kynurenic acid content.

| Loose preparations | Average | SD | SEM | Min. | Max. |
|---|---|---|---|---|---|
| Bebilon 1 Immuno fortis comfort | 0.33 | 0.12 | 0.07 | 0.20 | 0.45 |
| Bebilon AR 1 | 0.64 | 0.12 | 0.07 | 0.51 | 0.77 |
| Bebilon Junior 3 | 1.18 | 0.04 | 0.02 | 1.1 | 1.22 |
| Bebilon Junior 4 | 1.03 | 0.02 | 0.01 | 1.01 | 1.05 |
| Bebilon Pepti 2 | 0.38 | 0.08 | 0.05 | 0.33 | 0.47 |
| Bebilon 1 Immuno fortis | 1.08 | 0.16 | 0.09 | 0.98 | 1.27 |
| Bebilon 2 Immuno fortis | 0.99 | 0.36 | 0.21 | 0.7 | 1.4 |
| Bebilon 1 HA Immuno fortis | 0.21 | 0.05 | 0.03 | 0.18 | 0.28 |
| Bebilon HA 2 | 0.29 | 0.02 | 0.01 | 0.28 | 0.31 |
| Bebilon Comfort 2 | 0.47 | 0.27 | 0.16 | 0.3 | 0.78 |
| Bebilon Pepti 1 | 0.35 | 0.05 | 0.03 | 0.31 | 0.41 |
| Bebilon Nenatal premium | 0.85 | 0.29 | 0.16 | 0.64 | 1.18 |
| Bebiko 1 | 0.93 | 0.13 | 0.08 | 0.83 | 1.08 |
| Bebiko 2 | 0.71 | 0.02 | 0.01 | 0.69 | 0.73 |
| Bebiko 2R | 0.7 | 0.07 | 0.04 | 0.63 | 0.77 |
| Bebiko HA 1 | 0.25 | 0.01 | 0.01 | 0.23 | 0.27 |
| Bebiko HA 2 | 0.32 | 0.03 | 0.02 | 0.29 | 0.36 |
| Bebiko Junior 3 | 0.65 | 0.05 | 0.03 | 0.58 | 0.69 |
| Bebiko Junior 4 | 0.66 | 0.02 | 0.01 | 0.65 | 0.68 |
| Enfamil Premium 1 | 0.67 | 0.09 | 0.05 | 0.60 | 0.77 |
| Enfamil Premium 2 | 0.80 | 0.07 | 0.04 | 0.72 | 0.84 |
| Enfamil AR 1 | 0.89 | 0.07 | 0.04 | 0.83 | 0.96 |
| Enfamil AR 2 | 1.19 | 0.31 | 0.18 | 0.95 | 1.54 |
| HIPP Bio 1 | 1.03 | 0.05 | 0.03 | 0.99 | 1.08 |
| HIPP Bio 2 | 1.42 | 0.03 | 0.02 | 1.38 | 1.45 |
| HIPP Bio 3 | 1.52 | 0.23 | 0.13 | 1.28 | 1.74 |
| NAN 1 | 0.25 | 0.03 | 0.02 | 0.22 | 0.27 |
| NAN 2 | 0.54 | 0.10 | 0.06 | 0.43 | 0.64 |
| NAN HA 1 | 0.09 | 0.02 | 0.01 | 0.07 | 0.12 |
| NAN HA 2 | 0.31 | 0.10 | 0.06 | 0.19 | 0.40 |
| NAN HA 3 | 0.28 | 0.08 | 0.04 | 0.21 | 0.36 |
| NAN AR | 0.37 | 0.14 | 0.08 | 0.24 | 0.53 |
| NAN Active 1 | 0.24 | 0.05 | 0.03 | 0.20 | 0.30 |
| NAN Active 2 | 0.73 | 0.07 | 0.05 | 0.68 | 0.78 |
| NAN PRO d.night B | 0.95 | 0.14 | 0.08 | 0.77 | 1.05 |
| NAN PRO 3 | 0.98 | 0.05 | 0.03 | 0.93 | 1.03 |
| NAN 2 R | 0.71 | 0.37 | 0.21 | 0.33 | 1.06 |
| NAN 3 R | 1.08 | 0.11 | 0.02 | 1.08 | 1.08 |
| Nutramigen 1 hypoallergenic | 0.66 | 0.36 | 0.20 | 0.42 | 1.07 |

TABLE 3-continued

The concentration of kynurenic acid (µg/100 ml) in the tested milk preparations intended for feeding children with the indication of the series with the lowest and highest kynurenic acid content.

|  | | | | | |
|---|---|---|---|---|---|
| Nutramigen 2 hypoallergenic | 0.58 | 0.16 | 0.09 | 0.43 | 0.76 |
| Liquid preparations | Average | SD | SEM | Min. | Max. |
| Bebilon Nenatal premium | 0.74 | 0.02 | 0.01 | 0.72 | 0.75 |
| Bebilon Pepti liquid | 0.33 | 0.03 | 0.02 | 0.29 | 0.35 |
| Bebilon 1 | 0.44 | 0.08 | 0.05 | 0.39 | 0.53 |
| NAN PRO 1 | 0.31 | 0.04 | 0.02 | 0.29 | 0.36 |
| NAN PRO HA 1 | 0.07 | 0.01 | 0.01 | 0.06 | 0.07 |
| Enfamil Premium 1 | 0.51 | 0.02 | 0.01 | 0.49 | 0.53 |

SD-standard deviation;
SEM-standard error of the mean;
Min-average minimum value in the series;
Max-average maximum value in the series Example 3

Comparison of Kynurenic Acid Concentration in Commercial Preparations of Milk Intended for Child Nutrition with the Concentration in Human Breast Milk at the Same Time After Delivery In commercial preparations of milk intended for child nutrition in the period from birth, the average kynurenic acid content is very diverse and ranges from 0.03 to 1.08 µg/100 ml depending on the type of preparation, while the average content of kynurenic acid in breast milk on the third day after delivery is 0.39 µg/100 ml, on day 6, 1.07 µg/100 ml, at week 2, 2.11 µg/100 ml and week 4, 3.74 µg/100 ml. These amounts are significantly different from the amount of kynurenic acid in commercial preparations. There are also significant differences in the content of kynurenic acid between preparations from different production series. In addition, commercial preparations intended for children of this age contain a constant amount of kynurenic acid, whereas the content of kynurenic acid in breast milk increases almost 4 times in 4 weeks, from 0.39 µg/100 ml to 3.74 µg/100 ml. None of the products reflects the dynamics of changes in kynurenic acid content during this period.

In commercial preparations of milk intended for children from 4 months of age, the average content of kynurenic acid is 0.38 to 0.58 µg/100 ml depending on the type of preparation, while the average content of kynurenic acid in breast milk at 3 months after delivery is 4.15 µg/100 ml. This amount exceeds the amount of kynurenic acid in commercial preparations more than 10 times.

In commercial preparations of milk intended for child nutrition in the period from 6 months of age, the average kynurenic acid content is very diverse and ranges from 0.29 to 1.42 µg/100 ml depending on the type of preparation, while the average content of kynurenic acid in breast milk at 6 months after delivery is 5.66 µg/100 ml. This amount is much higher than the amount of kynurenic acid in commercial preparations appropriate to the age (4-20 times).

In commercial preparations of milk intended for child nutrition in the period from 9-24 months of age, the average kynurenic acid content is very diverse and ranges from 0.28 to 1.52 µg/100 ml depending on the type of preparation. These amounts are significantly lower than the average kynurenic acid content in mother's milk at 6 months after delivery, which is 5.66 µg/100 ml. This amount is much higher than the amount of kynurenic acid in commercial preparations appropriate to the age (4-20 times).

Example 4

The Preparation Method of Formula for Oral Feeding of Children

The solubility of kynurenic acid in water is 0.95 mg/ml (http://www.hmdb.ca/metabolites/HMDB00715).

Kynurenic acid is readily soluble in alkaline conditions; in 1.0 M NaOH, its solubility is 50 mg/ml (http://www4.mpbio.com/ecom/docs/proddata.nsf/440121766f8ee75e8525645d0068b043/2f736b86941e7f61852569cb00688812? OpenDocument).

There are salts of kynurenic acid which are well soluble in water, e.g. a sodium salt, with the solubility of 100 mM (http://www.abcam.com/kynurenic-acid-sodium-salt-ab120256.html), which corresponds to a solubility of 21 mg/ml.

The results of our own research in the light of data from the literature indicate that the solubility of kynurenic acid in water is sufficient to obtain the highest recommended concentration of this substance which results from the determination of the physiological content of kynurenic acid in the milk of breast-feeding women. The solubility of kynurenic acid of 0.95 mg/ml is 6900 times higher than the highest content of kynurenic acid in the mother's milk tested in the study, which is 13.78 µg/100 ml (Table 1), which allows the production of a preparation with an increased content of kynurenic acid in comparison to physiological contents. For this purpose, a well-soluble kynurenic acid salt or kynurenic acid dissolved in alkali may also be used.

Because kynurenic acid is soluble in water, kynurenic acid in powder form was added to the children's powder formula—Bebilon Nenatal in an amount corresponding to 10 times the highest content of kynurenic acid found in breast milk of 13.78 µg/100 ml (Table 1), that is 137.8 µg/100 ml converted into the volume recommended by the manufacturer. Then water was added in the amount recommended by the manufacturer and the whole was mixed well.

Macroscopic examination proved that the addition of kynurenic acid did not change the colour, consistency and pH of the mixture, compared to the control mixture, without the addition of kynurenic acid.

As nutritional preparations are available in ready liquid form, kynurenic acid dissolved in water was added to the finished liquid preparation Bebilon 1. The added amount of kynurenic acid corresponded to 10 times the highest content of kynurenic acid found in breast milk of 13.78 µg/ml (Table 1), that is 137.8 µg/100 ml.

Macroscopic examination proved that the addition of kynurenic acid did not change the colour, consistency and pH of the mixture, compared to the control mixture, without the addition of kynurenic acid. Conclusions: The preparation for oral feeding of children is prepared by means known in the food industry, provided that the kynurenic acid content should preferably be 0.01-0.7 µg/100 ml for children 1-5 days; 0.8-1.6 µg/100 ml for children aged 6-14 days; 1.7-2.9 µg/100 ml for children aged 2-3 weeks; 3.0-3.9 µg/100 ml for children aged 4-12 weeks; 4.0-5.0 µg/100 ml for children aged 4-6 months; 5.1-14.0 µg/100 ml for children aged 7-12 months.

SUMMARY

1. Human breast milk contains kynurenic acid in an increasing amount with breastfeeding time. Concentrations of kynurenic acid in milk of breastfeeding women are 14 times higher in the 6th month of feeding compared to 3 days after delivery.
2. The content of kynurenic acid in the majority of preparations for children's nutrition is significantly lower compared to the content of kynurenic acid in the milk of breast-feeding women. Only commercial preparations with the highest content of kynurenic acid contain kynurenic acid in the amount similar to the content in milk of women on day 6 of breastfeeding.
3. The content of kynurenic acid in infant preparations is accidental, i.e. it is not deliberately planned by the manufacturer and is not controlled.
4. The research results argue in favour of the development of a preparation refined formula intended for feeding children and offspring of mammals taking into account natural changes in the content of kynurenic acid in breast milk of women and lactating animals.
5. In order to obtain the desired effect of kynurenic acid, the content of kynurenic acid in infant preparations should preferably be 0.01-0.7 µg/100 ml for children aged 1-5 days; 0.8-1.6 µg/100 ml for children aged 6-14 days; 1.7-2.9 µg/100 ml for children aged 2-3 weeks; 3.0-3.9 µg/100 ml for children aged 4-12 weeks; 4.0-5.0 µg/100 ml for children aged 4-6 months; 5.1-14.0 µg/100 ml for children aged 7-12 months.
6. Due to the sufficiently good solubility of kynurenic acid in water ensuring its content at the physiological level, kynurenic acid or its soluble salt may be used to prepare the formula for feeding children and offspring of mammals in a loose form, or a solution of kynurenic acid or a salt thereof for preparation in a liquid form.

The invention claimed is:

1. A nutritional composition for the oral and enteral feeding of children comprising kynurenic acid or its salt designed for a child 4-12 weeks, wherein kynurenic acid or a salt thereof is present, in an amount of 3.0-3.9 µg/100 ml.

2. A nutritional composition for the oral and enteral feeding of children comprising kynurenic acid or its salt designed for a child aged 4-6 months, wherein kynurenic acid or a salt thereof is present, in an amount of 4.0-5.0 µg/100 ml.

3. A nutritional composition for the oral and enteral feeding of children comprising kynurenic acid or its salt designed for a child aged 7-12 months, wherein kynurenic acid or a salt thereof is present, in the amount of 5.1-14.0 µg/100 ml.

4. A nutritional composition for the oral and enteral feeding of children comprising kynurenic acid or its salt designed for a child aged 3 weeks, wherein kynurenic acid or a salt thereof is present in an amount of 1.7-2.9 µg/100 ml.

* * * * *